United States Patent [19]

Henderson et al.

[11] Patent Number: 4,793,987
[45] Date of Patent: Dec. 27, 1988

[54] STABILIZED RADIOLABELLED COMPOUNDS

[75] Inventors: Alan Henderson, Waedenswil, Switzerland; Kenneth S. Bowler, Buckinghamshire, Great Britain

[73] Assignee: Amersham International plc, Bucks, England

[21] Appl. No.: 856,019

[22] Filed: Apr. 25, 1986

[30] Foreign Application Priority Data

Apr. 26, 1985 [GB] United Kingdom ............... 8510726

[51] Int. Cl.$^4$ .................... A61K 49/02; G01N 33/48; G01N 33/50; C09K 15/30
[52] U.S. Cl. ......................................... 424/1.1; 436/8; 436/18; 252/645; 252/402; 252/403
[58] Field of Search ............... 424/1.1; 252/644, 645, 252/403, 402; 436/8, 18; 546/318, 321, 326, 341, 344, 339

[56] References Cited

U.S. PATENT DOCUMENTS

| | | | |
|---|---|---|---|
| 4,251,628 | 2/1981 | Ryan et al. | 424/1.1 |
| 4,358,434 | 11/1982 | Izodikov et al. | 424/1.1 |
| 4,390,517 | 6/1983 | O'Brien et al. | 424/1.1 |
| 4,411,881 | 10/1983 | Izodikov | 424/1.1 |
| 4,440,738 | 4/1984 | Fauzi et al. | 424/1.1 |
| 4,510,125 | 4/1985 | Grogg et al. | 424/1.1 |

OTHER PUBLICATIONS

Ostrovskii et al., CA 73:85172n (1970).
Tmenov et al., CA 90:202436r (1979).
CA 100: 140230h (1984).
Koyama, CA 83: 96435 (1975).

Primary Examiner—John F. Terapane
Assistant Examiner—J. E. Thomas
Attorney, Agent, or Firm—Wenderoth, Lind & Ponack

[57] ABSTRACT

A stabilizer for radioactively labelled organic compounds has the general formula

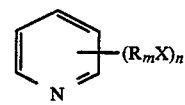

where R is C1 to C4 alkylene which may be OH substituted, m is 0 or 1 (i.e. R may be absent or present), X is carboxyl or sulphonyl e.g. COOH or $SO_3H$ or a salt thereof and n is 1, 2 or 3. Radiolabelled compounds of biological origin, such as nucleotides and amino acids, may be stabilized either in solution or in the freeze-dried state. For example, L-[$^{35}$S]methionine may be stabilized to prevent formation of a 47 KD band in protein transcription/translation experiments.

8 Claims, 1 Drawing Sheet

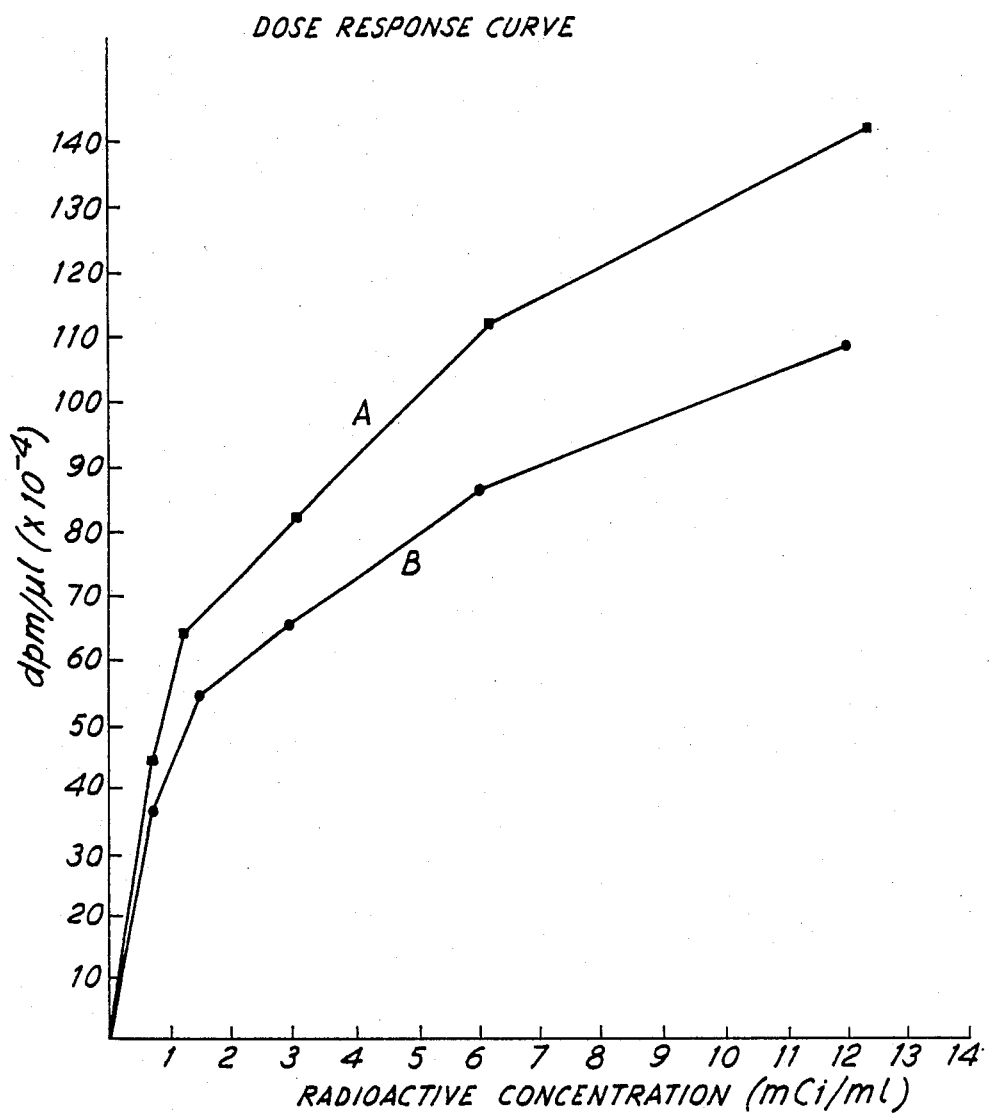

STABILIZED RADIOLABELLED COMPOUNDS

Radiolytic self-decomposition of radiochemicals has always been a problem to manufacturers and users alike. Shelf-life can be as little as a few weeks despite the use of the most suitable storage temperatures and physical dispersal methods for each particular compound or isotope as outlined in Review 16, Self-Decomposition of Radiochemicals. The Radiochemical Centre, Amersham.

A generally applicable additive which could be added to a radiochemical in order to extend shelf-life and improve its efficacy by minimising the formation of radioactive impurities would be of great economic and scientific value. A user of a stabilised radiochemical would find benefit from being able to conduct experiments over a longer time span, achieve more consistent results between batches of the same radiochemical and use less rigorous storage conditions. The additive should minimally interfere with or be compatible with the processes occurring in the application of radiochemicals to experimental systems typical of the intended use of such radiochemicals, for example the "in vivo" translation of protein using radiolabelled amino acids.

The methods which could be used to minimise self-decomposition of radiochemicals can be summarised as follows:

(a) Reduce the molar specific activity of the compound; but this may not be convenient for the intended use.

(b) Disperse the compound in a suitable medium, usually a solvent. Numerous solid diluents have been investigated, but are all inconvenient. Radiochemicals are often supplied in solution because this is the most convenient form for dispensing, and the rate of self-decomposition in solution can be altered by variations in the radioactive concentration. Although aromatic hydrocarbons, such as benzene, are regarded as the best protective solvents, unfortunately many compounds, particularly those of interest to biochemists and biologists, are soluble only in hydroxylic solvents and require the use of water, aqueous alcohol or similar mixtures for their storage.

(c) Add free radical scavengers to solutions. Numerous scavengers have been tested for their purpose, including benzyl alcohol, sodium formate, glycerol, cysteamine, ascorbic acid, mercaptoethanol, and ethanol. A scavenger needs to be chosen which is compatible both with the radiochemical and with the system in which it is to be used as a tracer, and this requirement makes the choice difficult. For example ethanol, which has been widely used as a free radical scavenger, has been reported to inhibit enzyme action.

(d) Store compounds at as low a temperature as possible, taking care to avoid the effects of molecular clustering. But storage at very low temperatures may be inconvenient.

(e) Use inhibitors against chemical decomposition. For example, buffers such as phosphate buffers, amine buffers and ammonium bicarbonate for nucleotides and nucleosides; but phosphate buffers interfere with phosphorylation reactions. Anti-oxidants have been used, for example butylated hydroxyanisole and butylated hydroxytoluene to stabilize vitamin A, and mercaptoethanol to stabilise methionine.

In practice none of these techniques are entirely effective by themselves, and combinations of them are generally used.

U.S. Pat. No. 4,390,517 describes the use of a wide variety of amines as stabilisers for solutions of radiolabelled compounds. Among the amines are included tertiary mono-amines of formula $RR^1R^2N$, where $R$, $R^1$ and $R^2$ are the same or different and are alkyl, cycloalkyl, alkenyl, hydroxyalkyl, aminoalkyl, thioalkyl, carboxyalkyl or keto alkyl of one to eight carbon atoms.

The present invention concerns a class of tertiary mono-amine stabilisers for radiolabelled compound which is not encompassed in the aforesaid U.S. Pat. No. 4,390,517. Our compounds have the advantage that they are capable of stabilising radiochemicals, not only in solution, but also in the solid e.g. freeze dried state.

The invention provides a composition comprising at least one radioactively labelled organic compound and a stabiliser thereof which stabiliser has the general formula

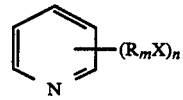

where
R is C1 to C4 alkylene which may be OH substituted
m is 0 or 1 (i.e. R may be absent or present)
X is carboxyl or sulphonyl e.g. COOH or $SO_3H$ or a salt thereof,
n is 1, 2 or 3.

The stabilisers are derivatives of pyridine containing 1, 2 or 3 (preferably 1 or 2) carboxyl groups, preferably COOH or soluble salt thereof such as potassium, sodium or ammonium salt. Examples of suitable stabilisers include:
2-pyridylacetic acid
Pyridine-3,4-dicarboxylic acid
Pyridine-2,5-dicarboxylic acid
2-pyridyl-hydroxymethane sulphonic acid.

It is well known that organic compounds labelled with different radioactive isotopes require protection in somewhat different ways, and may require different stabilisers. Examples of compositions according to this invention may contain radiochemicals labelled for example with 35-S, 3-H, 32-P, 33-P, 14-C, 125-I and 131-I.

This invention is applicable to radiolabelled compounds which are subject to radiolytic self-decomposition, for example:
Amino acids
Nucleotides
Thionucleotides
Nucleosides
Steroids
Lipids
Fatty acids
Peptides
Carbohydrates
Proteins
Nucleic acids The stabilisers minimise or eliminate the formation of decomposition products which can cause unwanted side reactions in experiments being performed. These side reactions could otherwise lead to the formation of radiolabelled compounds which may cause the experimenter to mis-interpret the results of an experiment. A particular problem arises in protein transcription/translation experiments using radiolabelled amino acids. One of the decomposition products of L-($^{35}$S)methionine appears to label the protein in rabbit reticulocyte lysate even in the absence of mRNA. This labelled product runs on an electrophoresis gel as a protein of 47 KD molecular weight. Although this artificial band is sometimes useful as a molecular weight marker, it may mask the presence of mRNA specific proteins which run in approximately the same position. The stabilisers of the present invention inhibit the radiolytic decomposition of L-($^{35}$S)methionine and therefore effectively reduce or prevent formation of this 47 KD band.

The compositions of the present invention may contain, in addition to radioactively labelled organic compound and stabiliser, other ingredients of known types. For example, buffers, anti-oxidants or free radical scavengers may be included in order to further reduce self-decomposition of the radiochemical. Other ingredients may be included as required for specific end uses of the radiochemical.

A radiochemical is generally supplied at a pH suitable to its intended use and having regard to its chemical nature. For example, most molecular biology/biochemical experiments are performed at around physiological pH. While the pH of compositions of this invention is not at all critical it is likely that most stabilised radiochemicals will be supplied at a pH in the range of 5 to 9.

In the compositions of this invention, the radiochemicals may be present in solution in any of the generally used solvents such as water, dilute mineral acid, dilute organic acid, ethanol, water/ethanol mixtures, or non-polar organic solvents such as benzene or toluene. Surprisingly, the radiochemicals may also be present in the solid, e.g. freeze-dried, state.

Storage of radiochemicals in the solid state, particularly at high specific activity, has often been felt to be undesirable because of the likelihood of rapid radiolytic self-decomposition. Traditional methods to overcome solid radiochemicals have involved dispersal on paper strips and other related procedures which cause inconvenience in both manufacture and use. Commonly used radical scavengers and anti-oxidants, such as ethanol and 2-mercaptoethanol, are volatile and are lost if freeze-drying is attempted.

The stabilisers of this invention have been found to be effective in reducing the rate of decomposition of radiochemicals in the solid state. This discovery was most unexpected and contrary to accepted thinking and practice by those experienced in the field. By supplying radiochemicals of the solid state the user has the means to dissolve the compounds in a solvent and at a concentration to suit his particular needs without the necessity to first remove the solvent in which the radiochemical would normally be supplied. Removal of solvent would be time consuming, potentially hazardous, and potentially injurious to the purity of the radiochemical. The user is free to choose a solvent in which the radiochemical would normally be considered to be prone to rapid decomposition and could thus not be supplied commercially. The stabilisers can be used either alone or together with non-volatile anti-oxidants such as dithiothreitol or ascorbic acid in order to increase the efficacy of the radiochemical for the user.

Increasing the concentration of the pyridine derivatives herein described increases their stabilising effect.

For radiochemicals in solution, a minimum stabiliser concentration of 1 mM is likely to be needed to produce a significant stabilising effect. A maximum limit on stabiliser concentration is set by the need to avoid affecting the experiment in which the radiochemical is to be used. When the intended use of the radiochemical is known, the optimum stabiliser concentration can readily be determined by routine trial. For general purpose use of radiochemicals in solution, stabiliser concentrations up to 300 mM are likely to be useful.

For compositions in the solid state, there are two ways of considering stabiliser concentration. One can consider the solution from which the freeze-dried composition is formed, and say that the stabiliser concentration in that solution should generally be from 1 to 300 mM. Or one can relate the stabiliser concentration to the activity of the radiochemical, and say that there should generally be present from 0.1 to 20 micromoles of stabiliser per millicurie of radiochemical.

For any particular radiochemical application, the stabiliser concentration should preferably be optimized with some care. In experiments involving the incorporation of radiolabelled amino acids into proteins, we have unexpectedly found that a correct choice of stabiliser concentration can enhance the degree of incorporation achieved compared to the same material without stabiliser. We are at present checking whether this surprising and advantageous finding is of general applicability.

The accompanying drawing in a graph showing Dose Response Curves more particularly described in Example 7.

The following examples illustrate the invention.

EXAMPLE 1

[Methyl-$^3$H]Thymidine at 40 Ci/mMol and 1 mCi/ml was stored at +4° C. in water in the presence of different stabilisers.

| Stabiliser | Purity at number of days stored | | | |
|---|---|---|---|---|
| | 0 | 13 | 42 | 65 |
| None | 96.9% | 93.3% | 65.1% | 55.1% |
| 50 mM, pH 7.5 2-Pyridylacetic acid K salt | 96.9% | 94.1% | 93.7% | 94.4% |
| 50 mM pH 7.5 Pyridine 3,4-dicarboxylic acid K salt | 96.8% | 97.7% | 94.8% | 94.8% |

EXAMPLE 2

L[$^{35}$S]Methionine at 1,200 Ci/mMol and 14 mCi/ml was stored at −20° C. in aqueous 0.1% 2-mercaptoethanol in the presence of different stabilisers.

| Stabiliser | Purity at number of days stored | | | |
|---|---|---|---|---|
| | 0 | 7 | 14 | 21 |
| None | 96% | 69% | 62% | 49% |
| 50 mM, pH 7.5 2-Pyridylacetic acid K salt | 96% | 91% | 87% | 86% |
| 10 mM pH 7.5 Pyridine 3,4-dicarboxylic acid K salt | 96% | 91% | 85% | 81% |

EXAMPLE-3

L-[35S]Methionine at 1300 Ci/mMol and 18 mCi/ml was stored at −20° C. in aqueous 0.1% 2-mercaptoethanol in the presence of stabilisers.

| Stabiliser | Purity at number of days stored | | |
|---|---|---|---|
| | 0 | 7 | 13 |
| None | 95% | 79% | 69% |
| 50 mM pH 7.5 Pyridine 2,5-dicarboxylic acid, K salt | 95% | 86% | 87% |
| 50 mM, pH 7.5 Pyridine 3,4-dicarboxylic acid K salt | 95% | 88% | 83% |

EXAMPLE 4

L-[35S]Methionine at 1250 Ci/mMol and 12 mCi/ml was stored at −80° C. in aqueous 0.1% 2-mercaptoethanol in the presence of different stabiliser concentrations.

| Stabiliser | Purity at number of days stored | | | | |
|---|---|---|---|---|---|
| | 0 | 12 | 20 | 25 | 31 |
| None | 99% | 95% | 92% | 87.5% | 86.5% |
| 10 mM, pH 7.5 Pyridine 3,4-dicarboxylic acid K salt | 96% | 94.5% | 94% | 93% | 95% |
| 50 mM, pH 7.5 Pyridine 3,4-dicarboxylic acid K salt | 97% | 97% | 99% | 98% | 96% |

EXAMPLE 5

L-[35S]Methionine at 1200 Ci/mMol was freeze dried in the presence of different stabilisers and stored at −80° C. Initial purity was 96%.

| Stabiliser | Purity after 7 days |
|---|---|
| None | 41% |
| 2-Pyridyl acetic acid, K salt | 94% |
| Pyridine 3,4-dicarboxylic acid, K salt | 89% |

Both stabilisers were present in the original solution at a concentration of 50 mM and the L-[35S]Methionine at 15.7 mCi/ml.

EXAMPLE 6

L-[35S]methionine at 1,300 Ci/mMol was freeze-dried in the presence of 2-Pyridylacetic acid, K salt at two different ratios and stored at −80° C. Initial purity was 95%.

| Stabiliser Concentration (micromoles per millicurie) | Purity at Number of days | | |
|---|---|---|---|
| | 14 | 26 | 36 |
| 3.4 | 93% | 92% | 90% |
| 1.7 | 91% | 85% | 82% |

EXAMPLE 7

Bioassay of L-[35S]methionine

Samples of L-[35S]methionine, with and without stabiliser were incorporated into protein using a system based upon rabbit reticulocyte lysate and employing Tobacco Mosaic Virus messenger RNA (TMV mRNA).

Each sample (about 0.6 mCi) was evaporated to dryness "in vacuo" and then dissolved in a rabbit lysate, water, cyclic AMP, TMV mRNA, premix at a radioactive concentration of about 12 mCi/ml. Serial dilutions of this initial concentration were made using further aliquots of the lysate premix. This gave a series of samples at reducing radioactive concentration which were all incubated at 30° C. for one hour. The samples were cooled on ice to stop reaction and equal sized aliquots withdrawn into a N/1 mixture of sodium hydroxide/hydrogen peroxide and incubated at 37° C. for 10 minutes to hydrolyse any L-methionyl-t-RNA complexes. Each sample was then treated with ice-cold 25% trichloroacetic acid to precipitate the radiolabelled proteins. The protein was isolated by filtration and washed with ice-cold 8% trichloroacetic acid to remove any unreacted L-[35S]methionine. The filter papers were dried, and incorporated radioactivity measured using a liquid scintillation counter. A graph of radioactive concentration against incorporated radioactivity was then constructed: this is called a dose response curve. The accompanying graph illustrates the higher level of incorporation achieved with stabilised L-[35S]methionine. Curve A gives results obtained using L-[35S]methionine solution stabilised with 15 mM pyridine-3,4-dicarboxylic acid, K salt at pH 7.5. Curve B gives results obtained using the solution without stabiliser.

EXAMPLE 8

Gel Electrophoresis of Proteins Synthesised using Rabbit Reticulocyte Lysate

One month old samples of L-[35S]methionine, without and with stabiliser at various concentrations and stored at −20° C. were incubated with a rabbit reticulocyte lysate, water, cyclic AMP, TMV mRNA premix. Some samples had the TMV mRNA omitted to give "blank" results; these should show no incorporation of radioactivity.

After incubation at 30° C. for 1 hour, aliquots were taken and boiled for 5 minutes with sodium dodecyl sulphate gel electrophoresis buffer to denature the synthesised proteins. Each sample was loaded onto a 15% Polyacrylamide Gel together with molecular weight markers and subjected to a constant voltage of 150 volts for about one hour. After drying, the gel was authoradiographed for up to 3 days. None of the stabilised L-[35S]methionine samples showed a band at 47 KD whereas the unstabilised L-[35S]methionine sample clearly showed a band in the "blank" sample at 47 KD.

EXAMPLE 9

[2-14C]Thymidine at 53 mCi/mMol and 50 uCi/ml was stored at +20° C. in water in presence of different stabilisers.

| Stabilizer | Purity at number of months stored | | |
|---|---|---|---|
| | 0 | 3 | 7 |
| None | 97.3% | 92.7% | 88.9% |

-continued

| Stabilizer | Purity at number of months stored | | |
|---|---|---|---|
| | 0 | 3 | 7 |
| 25 mM, pH 7.5 2-Pyridylacetic acid K Salt | 97.3% | 97.0% | 96.6% |
| 30 mM, pH 7.5 Pyridine 3,4 dicarboxylic acid K salt | 97.3% | 96.7% | 96.4 |

EXAMPLE 10

Adenosine 5'-1[γ-$^{32}$P]triphosphate at >5000 Ci/m-Mol and 10 mCi/ml was stored at −20° C. in aqueous 5 m molar 2-mercaptoethanol in the presence of different stabilisers.

| Stabilizer | Purity at number of days stored | | |
|---|---|---|---|
| | 0 | 8 | 15 |
| None | 83% | 84% | 75% |
| 30 mM, pH 7.5 Pyridine 3,4 dicarboxylic acid K salt | 86% | 83% | 83% |
| 30 mM, pH 7.5 2-Pyridylhydroxymethane sulphonic acid K salt | 85% | 83% | 83% |

We claim:

1. A composition comprising at least one radioactivity labelled organic compound selected from the group consisting of amino acid or nucleotide and a stabiliser therefor which stabiliser has the general formula

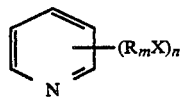

where
R is C1 to C4 alkylene which may be OH substituted
m is 0 or 1
X is carboxyl or sulphonyl or a salt thereof,
n is 1, 2 or 3.

2. The composition as claimed in claim 1, wherein the stabiliser is selected from 2-pyridylacetic acid, pyridine-3,4-dicarboxylic acid, pyridine-2,5-dicarboxylic acid, 2-pyridyl-hydroxymethane sulphonic acid and salts thereof.

3. The composition as claimed in claim 1, wherein the radioactive label is selected from 35-S, 3-H, 32-P and 14-C.

4. The composition as claimed in claim 1, wherein the radioactively labelled organic compound is L-($^{35}$S)methionine.

5. The composition as claimed in claim 1, wherein the labelled organic compound is present in solution.

6. The composition as claimed in claim 5, wherein the concentration of stabilizer is from 1 to 300 mM.

7. The composition as claimed in claim 1, wherein the labelled organic compound is present in the freeze-dried state.

8. The composition as claimed in claim 7, wherein from 0.1 to 20 micromoles of stabilizer is present per millicurie of labelled organic compound.

* * * * *